United States Patent [19]
Falco

[11] Patent Number: 6,148,821
[45] Date of Patent: Nov. 21, 2000

[54] SELECTIVE NONLINEAR ATTENUATING EARPLUG

[75] Inventor: Robert N. Falco, Indianapolis, Ind.

[73] Assignee: Cabot Safety Intermediate Corporation, Southbridge, Mass.

[21] Appl. No.: 09/069,108

[22] Filed: Apr. 29, 1998

[51] Int. Cl.[7] .................................................. A61F 11/00
[52] U.S. Cl. .......................................... 128/864; 128/867
[58] Field of Search .................................. 128/864–868; 181/131, 135

[56] References Cited

U.S. PATENT DOCUMENTS

| | | | |
|---|---|---|---|
| 3,800,791 | 4/1974 | Visor | 128/864 |
| 4,540,063 | 9/1985 | Ochi | 181/135 |
| 4,867,149 | 9/1989 | Falco | 128/864 |
| 5,113,967 | 5/1992 | Killion | 181/135 |

FOREIGN PATENT DOCUMENTS

| | | |
|---|---|---|
| E89153 | 5/1993 | Austria . |
| 4217043 A1 | 11/1992 | Germany . |
| WO 91/11160 | 8/1991 | WIPO . |

*Primary Examiner*—Michael A. Brown
*Attorney, Agent, or Firm*—Cantor Colburn LLP

[57] ABSTRACT

The present invention presents a selective nonlinear attenuating earplug. The earplug is tunable by the wearer and permits the wearer to select the performance of the earplug. The earplug of the present invention can function either in a selective attenuation mode or a maximum attenuation mode. The selective capability of the earplug permits a wearer to select the degree of desired sound attenuation depending upon the particular environment surrounding the wearer. In the selective attenuation mode, sound attenuation is low for a specific range of intensities and increases for sounds with intensity above those in the specified range. Selective attenuation is especially effective for the loudest noises. The advantage of a selective attenuation mode is especially realized when the wearer wishes to receive an intelligible speech transmission while being situated in a noisy environment while still protecting the wearer from dangerous noises. The present invention is particularly useful when the noisy environment is caused by high continuous or pulsed noises, such as gunshots or those noises generated in an industrial setting. In the maximum attenuation mode, the hearing protector stops all sounds throughout the frequency range, regardless of their intensity.

27 Claims, 4 Drawing Sheets

SELECTIVE NONLINEAR ATTENUATING EARPLUG

BACKGROUND OF THE INVENTION

1. Field of the Invention

This invention relates generally to hearing protective earplugs and is more specifically directed to a selective nonlinear attenuating earplug construction useful as a hearing protector.

2. Brief Discussion of the Prior Art

Environmental sounds are typically comprised of a mixture of various sound wave frequencies having varying intensities. It is well documented that repeated or prolonged exposure to sounds of sufficiently high sound pressure level will cause temporary or permanent hearing loss. For example, exposure to sound waves of some frequencies and of varying intensities under conditions of severe impact can damage the auditory organ and cause serious hearing problems, including deafness. Injurious noises such as those caused by explosions or bursts are often comprised of a mixture of sound wave frequencies of varying intensity. These disturbing frequencies are in both the high and low frequency bands and have an intensity sufficient to cause hearing problems. Individuals who are frequently exposed to sound having such disturbing and sometimes dangerous frequencies and intensities run the risk of incurring such injuries as hearing loss or even deafness. These individuals include workers at demolition or construction sites, operators of heavy, noisy equipment and those in active military service. Ear (i.e. hearing) protection is needed to prevent a loss in hearing acuity and the gradual increase in the threshold of hearing resulting from extended exposures to loud noise.

Sound attenuation devices are known which specifically address this problem. These include conventional earplugs, earmuffs, and the like which function to reduce the negative effects of exposure to dangerous frequencies by limiting the entry of all sound waves into the auditory organ. Sound attenuation devices may be either linear or nonlinear in nature. Linear attenuation devices attenuate sound at a predetermined level regardless of the frequency of the sound, while nonlinear devices attenuate sound at different levels have depending upon the frequency of the sound. These conventional devices suffer from a significant disadvantage, namely that auditory access to environmental sounds of relatively risk free frequencies is also limited. Thus, the devices suffer from the limitation that they provide much greater attenuation at high frequencies than at low frequencies and/or provide excessive attenuation at high frequencies. The result is that the wearer of these devices who wanted or needed to hear clearly was prevented from doing so. Therefore, while these devices were protective to some extent against the effects of overexposure to sound having dangerous frequencies and intensities, they in themselves created a new danger in that they shut out all environmental sounds including those of speech and warning.

Devices designed to increase the audibility of earplugs are known in the art. For example, in U.S. Pat. No. 4,540,063 to Ochi et al., there is disclosed an earplug construction capable of attenuating sound waves of multiple frequencies. The earplug comprises an outer shell having inlet and outlet apertures at opposite ends and containing a sound wave attenuation unit disposed between the apertures such that environmental sound waves enter the earplug through the inlet aperture, penetrate the sound wave attenuating unit wherein sound waves are attenuated and exit the earplug through the outlet aperture. The sound wave attenuating unit is composed of a first and a second plate of a sound absorbing material positioned near the inlet and outlet apertures respectively and a pair of thin sheets of a fabric having substantially uniform air permeability and elasticity disposed therebetween and forming an air chamber between the sheets.

In U.S. Pat. No. 5,113,967 to Killion et al., there is disclosed an earplug construction for improved audibility. The earplug comprises an eartip portion arranged for positioning with at least an inner end portion thereof in an ear canal to define a first sound passage extending from an inner end within the ear canal to an opposite outer end, and in which a second sound passage is formed by a structure which is preferably external to the ear canal, the second sound passage having an inner end coupled to the outer end of the first passage and having an opposite sound-receiving outer end. An important feature is that the second passage includes a portion folded back on itself. Through the use of an earplug construction in which an assembly contains an acoustic damper between two sound channels, the first being the sound tube internal to the eartip and the second being external folded back portion, the attenuation of sound waves is realized.

By providing a selective attenuation mode, the earplug can offer the wearer the ability to choose between two different performance settings for the earplug depending upon the exact environment in which the wearer intends to use the earplugs. In the selective mode, sound attenuation is low for a specific range of intensities above those in the specified range. Selective attenuation is especially effective for the loudest noises. A sample application of the earplug in the selective attenuation mode is the intelligible speech transmission in a noisy environment caused by pulsed noises, such as gunshots, for example. In the maximum attenuation mode, the earplug stops all sounds throughout the intensity range, regardless of their intensity.

While suitable for their intended purpose, there is a perceived need for a more effective and improved earplug device whereby the earplug offers different levels of attenuation and is sized to fit most ears. The selective attenuation earplug devices of the prior art suffer from the disadvantage that these earplugs are not particularly well suited for environments where selective attenuation and maximum attenuation is desired and the capability of easily and quickly interchanging the device from one mode to another is desired.

SUMMARY

The above-described drawbacks and deficiencies of the prior art are alleviated by the earplug of the present invention, wherein a selective nonlinear attenuating earplug is provided. The present invention is directed towards an improved earplug wherein the earplug is tunable by the wearer and permits the wearer to select the performance of the earplug. The earplug of the present invention can function either in a selective attenuation mode or a maximum attenuation mode. The selective capability of the earplug permits a wearer to select the degree of desired sound attenuation depending upon the particular environment surrounding the wearer. In the selective attenuation mode, sound attenuation is low for a specific range of intensities and increases for sounds with intensity above those in the specified range. Selective attenuation is especially effective for the loudest noises. The advantage of a selective attenuation mode is especially realized when the wearer wishes to receive an intelligible speech transmission while being situated in a noisy environment while still protecting the wearer from dangerous noises. The present invention is particularly useful when the noisy environment is caused by high continuous or pulsed noises, such as gunshots or those noises generated in an industrial setting. In the maximum attenuation mode, the hearing protector stops all sounds throughout the frequency range, regardless of their intensity.

The earplug of the present invention overcomes problems associated with the prior art by permitting those in the military or those working in a loud industrial setting to be able to communicate between themselves all while protecting their hearing against sudden noises, especially the noise of weapons or machinery with high levels of noise. The above-discussed and other features of the present invention will be appreciated and understood by those skilled in the art from the following detailed description and drawings.

BRIEF DESCRIPTION OF THE DRAWINGS

For the purpose of illustrating the invention, there are shown in the drawing forms which are presently proffered; it being understood, however, that this invention is not limited to the precise arrangements and instrumentalities shown. Referring now to the drawings wherein like elements are numbered alike in the several FIGURES.

DETAILED DESCRIPTION OF THE INVENTION

The present invention is directed towards an improved earplug wherein the earplug is tunable by the wearer and permits the wearer to select the performance of the earplug. The earplug of the present invention can function either in a selective attenuation mode or a maximum attenuation mode. The selective capability of the earplug permits a wearer to select the degree of desired sound attenuation depending upon the particular environment surrounding the wearer. In the selective attenuation mode, sound attenuation is low for a specific range of intensities and increases for sounds with intensity above those in the specified range. Selective attenuation is especially effective for the loudest noises. The advantage of a selective attenuation mode is especially realized when the wearer wishes to receive an intelligible speech transmission while being situated in a noisy environment while still protecting the wearer from dangerous noises. The present invention is particularly useful when the noisy environment is caused by high continuous or pulsed noises, such as gunshots or those noises generated in an industrial setting. In the maximum attenuation mode, the hearing protector stops most sounds throughout the frequency range, regardless of their intensity.

In accordance with the present invention, the earplug comprises a stalk member and a stem. The stalk member is an elongated member having a passage way therethrough, wherein the passage way runs from a nose end of the stalk to a cavity formed in the stalk member. At said opposite end, the cavity has an increased inner dimension compared to the stalk passage way thereby forming a shoulder wherein the passage way communicates with the cavity. The shoulder of the stalk member supports the stem and positions the stem relative to the stalk so that the stem abuts the shoulder and is prevented from traveling into the stalk passage way. The stalk cavity is sized so as to receive the stem therein, whereby the stem is inserted until the stem contacts the stalk shoulder which acts as a stop.

The stem is an elongated member having a stem cavity at one end and a free end at the opposite end of the stem. The stem also includes a passage way which runs from one end of the stem cavity and terminates within the body of the stem. The stem cavity has an increased dimension relative to the stem passage way and therefore forms a stem shoulder where the cavity and passage way communicate with one another. The stem cavity is sized to receive the acoustic filter and permit the acoustic filter to be easily inserted and removed from said cavity. The acoustic filter rests on the stem shoulder and is axially aligned with the stem cavity.

The acoustic filter is provided within the stem and rests on the shoulder of the stem. The cavity and shoulder of the stem positions the acoustic filter relative to the stem. In particular, the acoustic filter is positioned so that it is axially aligned with both the stem passage way and the stalk passage way.

The stem is rotatably coupled with the stalk member by positioning the stem within the cavity of the stalk member so that the cavity portion of the stem abuts the shoulder of the stalk member. When the stem is rotatably coupled with the stalk member, a sound channel is formed. The sound channel is formed by the stalk passage way, the stem passage way and the acoustic filter and runs from the nose end of the stalk member and terminates within the body of the stem.

Sound enters the sound channel from the environment by means of an inlet aperture defined by a stem aperture and a stalk aperture. The inlet aperture is functional only when the stem aperture and the stalk aperture are axially aligned thereby permitting sound waves to pass through the inlet aperture and into the sound channel. The inlet aperture is essentially perpendicular to the longitudinal axis of the sound channel.

By being rotatably coupled to the stalk, the stem regulates the sound channel in that the rotation of the free end of the stem opens or closes the inlet aperture. When the wearer desires for the earplug to be in a selective attenuation mode, the wearer simply causes the stem aperture to be aligned with the stalk aperture thereby permitting sound waves to enter the sound channel through the inlet aperture. In this mode, sound waves enter the inlet aperture and travel into the sound channel. By being positioned in the cavity of the stem and resting between the shoulder of the stalk member and the shoulder of the stem, the acoustic filter forms a part of the sound channel so that sound waves traveling within the sound channel enter the acoustic filter. As sound waves travel into the acoustic filter, the sound waves are effectively attenuated by the acoustic filter before continuing along in the sound channel and finally exiting the earplug and traveling into the wearer's ear canal.

When the wearer desires the earplug to function in a maximum attenuation mode, the wearer prevents sound waves from entering the sound channel by closing the sound channel by turning the free end of the stem 90° within the stalk member thereby causing the stem aperture to be skewed from the stalk aperture. By preventing sound waves from entering the inlet aperture, the earplug effectively limits the entry of all sound waves into the auditory organ. Such a mode may be desired when the wearer wishes maximum protection against all environmental sounds and at the same time does not wish to receive clearly sounds having low intensities.

The stalk member and stem also act as a stiffener to aid insertion of the earplug into the ear of the wearer. The stalk member is an elongate member which can be of any convenient length such that the free end of the stem body extends beyond the stalk body when the stem is coupled with the stalk member and the sound channel is of sufficient length so that the acoustic filter may be provided within the cavity of the stem body and the acoustic filter communicates with the sound channel so that sound waves may enter through the inlet aperture, penetrate the acoustic filter and then exit the earplug through the sound channel and enter the ear canal.

In accordance with the present invention, the selective nonlinear attenuating earplug of the present invention may comprise a variety of forms and may be composed of any suitable material for earplug constructions. For example, in one embodiment, the earplug of the present invention comprises a resilient polymeric multiple flange earplug construction as disclosed in U.S. Pat. No. 4,867,149, which is herein incorporated by reference in its entirety. In another embodiment, the eartip portion of the earplug of the present invention may be made of a premolded polymeric foam composed of resilient polymer foam materials such as foam rubber, polyurethane, or plasticized polyvinylchloride. For instance, in U.S. Pat. No. 5,188,123, which is herein incorporated by reference in its entirety, there is disclosed a premolded, polymeric foam eartip portion of an earplug of the push-in type which is suitable for use in the present invention.

Figure 1:
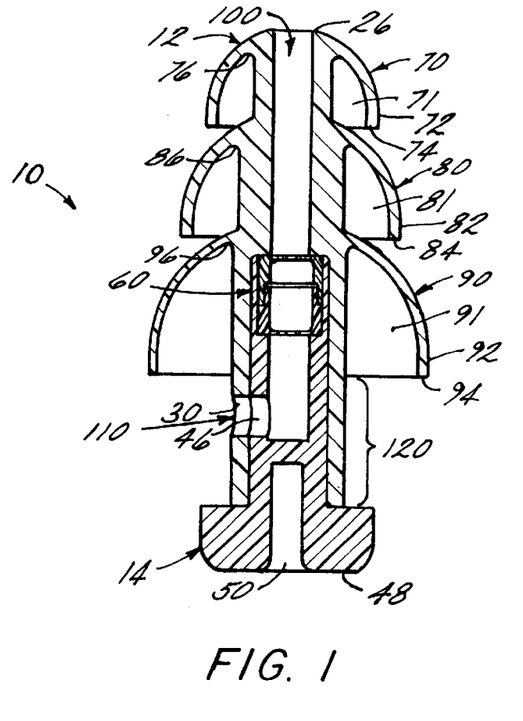
FIG. 1 is a cross-sectional view of one embodiment of the selective nonlinear attenuating earplug in accordance with the present invention.
Figure 2:
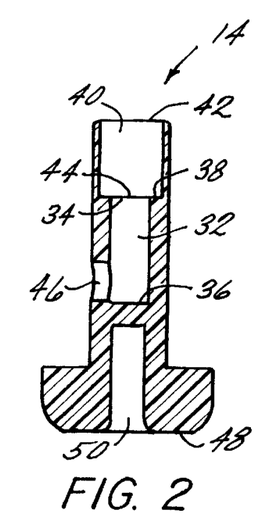
FIG. 2 is a cross-sectional view of the stem of the earplug of FIG. 1.
Figure 3:
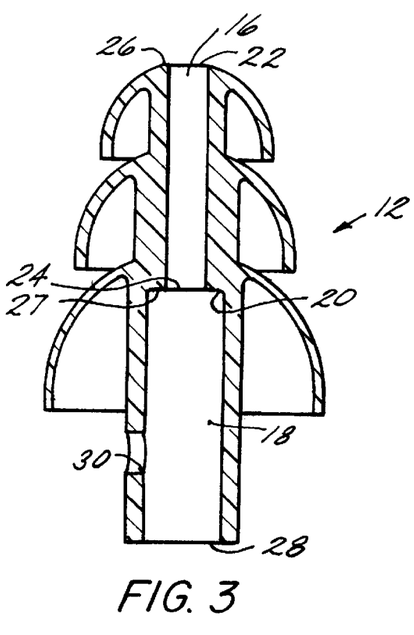
FIG. 3 is a cross-sectional view of the stalk member of the earplug of FIG. 1.

Now turning to FIGS. 1–3 wherein one embodiment of the selective attenuation earplug of the present invention is provided and is generally designated by reference numeral 10. Earplug 10 of this embodiment broadly comprises a stalk member 12, a stem 14, an acoustic filter 60 and an array of at least three rearwardly orientated and spaced apart flange elements 70, 80, and 90, each being of generally circular cross section. Preferably each flange element of the array extends rearwardly from its point of attachment to stalk member 12. It is within the scope of this invention that earplug 10 may comprise at least one flange extending from stalk member 12 wherein the flanges have a conical or arcuate shape.

Earplug 10 includes a stalk member 12. Stalk member 12 consists of an elongated member having a stalk passage way 16, a stalk cavity 18, and a shoulder 20. Stalk passage way 16 is axially aligned with stalk cavity 18. Stalk passage way 16 has a first end 22 and a second end 24, first end 22 being at a nose end 26 of stalk member 12. Second end 24 is proximate stalk cavity 18 and axially aligned with stalk cavity 18 so that stalk passage way 16 communicates with stalk cavity 18. Stalk cavity 18 has a first end 26 which abuts annular shoulder 20 and a second end 28 which receives stem 14. Stalk cavity 18 at said first end 26 abuts annular shoulder 20 which is formed by stalk member 12. Stalk member 12 also includes a stalk aperture 30.

Stem 14 is an elongated member and has a stem passage way 32, a stem cavity 40, and an annular shoulder 38. Stem passage way 32 has a first end 34 and a second end 36 wherein first end 34 communicates and is axially aligned with stem cavity 40. Second end 36 of stem passage way 32 terminates within the body of stem 14. First end 42 of stem cavity 40 receives acoustic filter 60 and second end 44 is axially aligned and communicates with stem passage way 32. At second end 44 of stem cavity 40 annular shoulder 38 is provided to position acoustic filter 60. Stem cavity 40 is sized to receive acoustic filter 60 and when acoustic filter 60 is inserted into stem cavity 40, acoustic filter 60 rests on annular shoulder 38 thereby axially aligning the acoustic filter with stem passage way 32.

Figure 8:
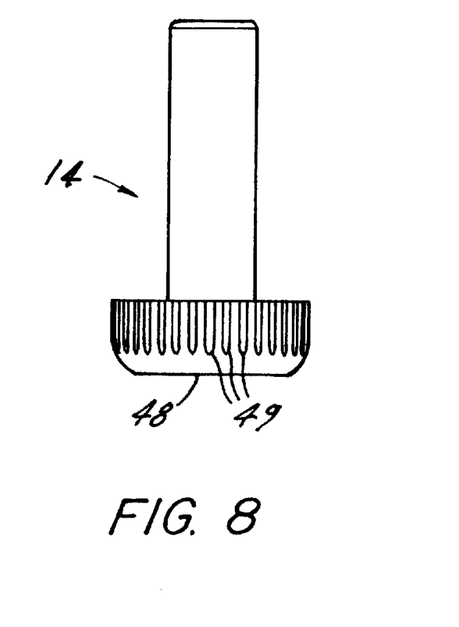
FIG. 8 is a perspective view of one embodiment of the stem; wherein the free end of the stem has ribs.

Stem 14 also includes a stem aperture 46 and a free end 48 opposite stem cavity 40. At free end 48, stem 14 may contain an axially orientated channel or aperture 50 of a size adapted to receive the end of a length of pliant cord therein. The pliant cord may be used to conventionally hold together the two earplugs. Free end 48 has an outer dimension (e.g. diameter) greater than the outer dimension of stalk member 12. This facilitates grasping stem 14. As shown in FIG. 8, free end 48 may also have ribs 49 to facilitate rotating stem 14.

Stem 14 is rotatably coupled with stalk member 12 by inserting first end 42 of the stem cavity 40 into stalk cavity 18 until first end 42 of stem cavity 40 contacts annular shoulder 20 of stalk member 12. When first end 42 of stem cavity 40 abuts annular shoulder 20 of stalk member 12, annular shoulder 20 acts as a stop and positions acoustic filter 60 within stem cavity 40 and relative to stem passage way 32 so that both are axially aligned with stalk passage way 16 thereby forming sound channel 100 of the present invention. When stem 14 is properly inserted into cavity 18 of stalk member 12 then the acoustic filter 60 is positioned between annular shoulder 20 of stalk member 12 and annular shoulder 38 of stem 14.

Sound channel 100 is a contiguous channel formed by stalk passage way 16, stem passage way 32, and acoustic filter 60. Preferably, stalk passage way 16, stem passage way 32, stalk cavity 18 and stem cavity 40 are cylindrical in nature; however, it is within the scope of this invention that the passage ways and cavities may take the form of other suitable shapes and dimensions. In an exemplary embodiment, the diameter of stalk passage way 16, stem passage way 32, stem aperture 46, sound channel 100 and inlet aperture 110 is between about 0.073 inches to about 0.076 inches.

Selective attenuation earplug 10 of the present invention also includes inlet aperture 110 which permits sound waves to enter sound channel 100 from the environment. Inlet aperture 110 is defined by stalk aperture 30 and stem aperture 46 and is functional only in a first orientation when stalk aperture 30 and stem aperture 46 are axially aligned thereby permitting sound waves to travel into sound channel 100. Inlet aperture 110 is generally perpendicular to sound channel 100.

By being rotatably coupled to stalk member 12, stem 14 regulates the sound channel 100 in that rotation of free end 48 of stem 14 opens or closes inlet aperture 110. When the wearer desires for earplug 10 to be in selective attenuation mode, the wearer simply causes stem aperture 46 to be axially aligned with stalk aperture 30 thereby creating a functional inlet aperture 110. In the first orientation when inlet aperture 110 is functional, sound waves are permitted to enter through inlet aperture 110 and travel into sound channel 100. Because stalk passage way 16, stem passage way 32 and acoustic filter 60 are all axially aligned with respect to one another to form sound channel 100, sound waves entering sound channel 100 through inlet aperture 110 travel through sound channel 100 and enter acoustic filter 60 wherein the sound waves are attenuated. Sound waves exit acoustic filter 60 and travel through sound channel 100 and into the ear canal of the wearer.

In a second orientation when the wearer desires earplug 10 to function in a maximum attenuation mode, the wearer prevents sound waves from entering sound channel 100 by closing the sound channel 100 by turning free end 48 of stem 14 ninety degrees (90°) relative to stalk member 12 thereby causing stem aperture 46 to be skewed from stalk aperture 30. By preventing sound waves from entering inlet aperture 110, earplug 10 effectively limits the entry of all sound waves into the eardrum. Such a mode may be desired when the wearer wishes maximum protection against all environmental sounds and at the same time does not wish to clearly receive sounds having low intensities.

Figure 4:
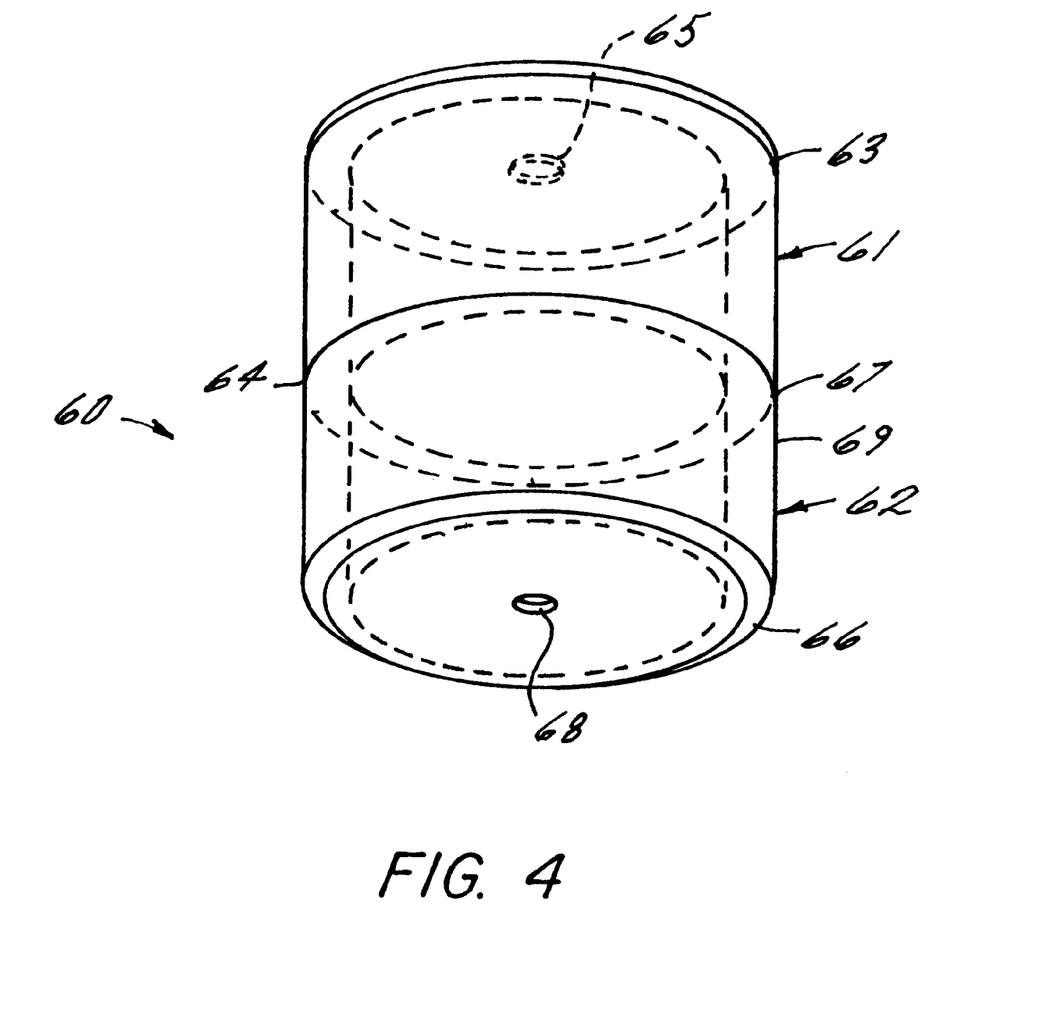
FIG. 4 is a perspective view of one embodiment of an acoustic filter of the present invention for use with the earplug of FIG. 1.

Acoustic filter 60 comprises an acoustic filter which attenuates sound and which is suitable for use in a selective attenuation plug. In accordance with the present invention, any suitable acoustic filter may be used with earplug 10. Shown in FIG. 4 is one embodiment of an acoustic filter suitable for use in the selective attenuation earplug of the present invention. Generally, the acoustic filter of this embodiment consists of a tube containing two rigid disks spaced axially opposite each other at a distance between about 2 mm and about 7 mm. Each of these disks contain at least one opening to permit sound waves to travel into and out of the acoustic filter resulting in the attenuation of the sound waves. Acoustic filter 60 comprises a first hollow cylindrical member 61 and a second hollow cylindrical member 62. First cylindrical member 61 has a first end 63 and a second end 64. First cylindrical member 61 is closed at said first end 63 by a disk containing a central orifice 65. At second end 64, first cylindrical member 61 is open whereby the periphery edge of second end 64 contains a shouldering wall 69. Second cylindrical member 62 includes a first end 66 and a second end 67, wherein second cylindrical member 62 is open at second end 67 and closed at first end 66 by a disk containing a central orifice 68. In an exemplary embodiment, the diameter of central orifices 65, 68 is about 3 mm. The periphery edge of second end 67 of second cylindrical member 62 contains a shouldering wall 69. The two complimentary open second ends 64,67 are coupled together by conventional means of fixation. One or both of the disks used in this embodiment to enclose one end of a cylindrical member may be positioned at a distance from the respective end of the tube forming the acoustic filter 60.

Referring to FIG. 1, earplug 10 includes an array of at least three rearwardly orientated and spaced apart flange elements 70, 80, and 90, each being of generally circular cross section and are provided on the stalk member. In another embodiment, earplug 10 comprises at least one rearwardly orientated flange member wherein the flanges have a hemispherical, conical or arcuate shape. Preferably, each flange element of the array extends rearwardly from its point of attachment to stalk member 12 in a convexly arcuate manner. The earplug of the present invention can be fabricated by any suitable polymer molding technique, such as by injection molding thereof. Flange elements 70, 80, 90 have skirts 72, 82, 92 respectively, composed of a suitable resilient polymeric material, as disclosed in U.S. Pat. No. 4,867, 149. The stalk member and stem may be composed of a resilient polymeric material of the same type employed for flange skirts 72, 82, 92 or, if desired, can be composed of another suitable resilient polymeric material. In one preferred embodiment, however, for purposes of easy fabrication, it will be preferred to utilize a single polymeric material for the entirety of the construction.

There are many known resilient polymeric materials which may be utilized effectively in the fabrication of the earplugs of the present invention. For instance, natural rubber, neoprene rubber, SBR rubber, silicone rubber, EPDM rubber, polybutadiene rubber, polyurethane elastomers, ethylene vinyl acetate elastomers, elastomers based on acrylic acid precursors and vinyl halide polymers are all generally suitable materials for construction which can generally be procured from commercial sources. Particularly preferred polymeric materials are the thermoplastic compositions such as exemplified by a family of thermoplastic injection moldable elastomers sold under the trademark, C-FLEX®, Concept Polymer Technologies, Inc., Largo, Fla. These thermoplastic compositions are available in a considerable range of Shore A Durometer hardness values. These compounds can be thermally formed into intricate shapes by any conventional thermoplastic molding technique. Earplugs produced can generally be sterilized or cleansed without degradation thereof. Another preferred material of construction of the earplugs of the present invention is a thermoplastic SBR block copolymer such as produced and sold in a number of grades under the brand name KRATON, by Shell Chemical Company, Synthetic Rubber Division, NY, N.Y.

First flange 70 extends outwardly and rearwardly from nose end 26 of stalk member 12 thereby to define a uniformly thin skirt 72 which is spaced apart along its length from that portion of stalk member 12 lying thereunder. Second flange element 80 extends outwardly and rearwardly from a first intermediate location along the length of stalk member 12 thereby to define a uniformly thin skirt 82 which is spaced apart along its length from that portion of stalk member 12 lying thereunder. Similarly, third flange element 90 extends outwardly and rearwardly from a second intermediate location along the length of stalk member 12, thereby to define a uniformly thin skirt 92 which is spaced apart along the length of stalk member from that portion of stalk member 12 lying thereunder. As will be noted from the drawing, root portions 76, 86 and 96 of flange skirts 72, 82 and 92 respectively, in other words, the points of juncture of the interior surfaces of the skirts with stalk member 12, are preferably conformed so as to provide minimum radiusing therebetween consistent with good molding practices, thereby to minimize thickening and consequential stiffening of the material of construction at said points. This design feature of the construction not only assures that skirts 72, 82 and 92 are afforded maximum flexibility at said root portions, but also provides skirts 72, 82, and 92 with a desirable "over center" eversion capability whereby each skirt is manipulated so as to be everted from its normally rearwardly directed orientation to a more forwardly directed orientation. When so forwardly everted, the interior surfaces of the skirts and the portions of stalk member 12 normally underlying the skirts are exposed, thereby affording the user the ability to readily inspect and/or cleanse areas of the earplug normally hidden from view.

The diameter of that portion of the stalk member underlying each of skirts 72, 82 and 92, respectively, is selected such as to provide an annular free space 71, 81 or 91 thereunder and into which free space the skirt is enabled to deflect during insertion of the earplug into the ear canal. The specific dimensions of annular free spaces 71, 81 and 91 are not particularly critical provided, of course, that each be adequate to serve the foregoing function. It is, however, generally desireable that each said annular free space have a dimension thereacross, determined by subtracting the diameter of the underlying stalk member from the internal diameter of the open end of the skirt and dividing the result by two, of at least twice the thickness of the particular skirt 72, 82 or 92 disposed thereover. By "annular free space", it is meant that the annular space 71, 81 or 91 contain no element or material therein which would tend to obstruct or restrict the movement of the associated skirt thereinto.

In order that the earplug of the present invention can be readily inserted and removed from the ear canal, it is desireable that stalk member 12 extend rearwardly to any convenient length beyond the trailing edge 94 of the rearmost flange element 90 such that the rearmost portion defines a handle 120 to be readily grasped between the thumb and the forefinger of the user.

It is often desireable to provide a pair of earplugs tethered together by means of a length of plaint cord. Such a tethered earplug construction can serve to prevent accidental dropping or loss thereof. This can be of importance, for instance, where the earplugs are to be utilized in an industrial food processing environment or in an environment wherein a dropped earplug would be likely to be so dirtied as to be rendered unusable or to be lost altogether. In order to provide such a tethered earplug construction, free end 48 of stem 14 can be provided with an axially orientated channel or aperture 50 of a size adapted to receive the end of a pliant cord (not shown) therein. The cord can be secured in channel 50 by any suitable means, such as by use of a suitable solvent or thermal welding thereof or by use of a suitable adhesive or by use of a cord whose ends are of somewhat greater diameter than the diameter of receiving channel or aperture 50, thereby to cause the resilient polymeric material surrounding channel or aperture 50 to resiliently grasp the cord ends in a secure manner. Channel or aperture 50 may also comprise a tapered channel of a size adapted to receive the end of the pliant cord.

A preferred pre-molded three-flange stalk member is commercially available from Aearo Company under the trade name "ULTRAFIT", in which the stalk passage way and stalk cavity are provided by molding a passage and cavity of suitable dimension through the center of the stalk member along its axis. Such molding techniques are known in the relevant art and any suitable conventional molding techniques may be used to produce stem 14 and stalk member 12 of the present invention. Stem 14 and stalk member 12 of the present invention may be manufactured by using the procedures and details disclosed in U.S. Pat. No. 4,867,149, and preferably stem 14 and stalk member 12 are composed of the same resilient polymeric material.

Figure 5:
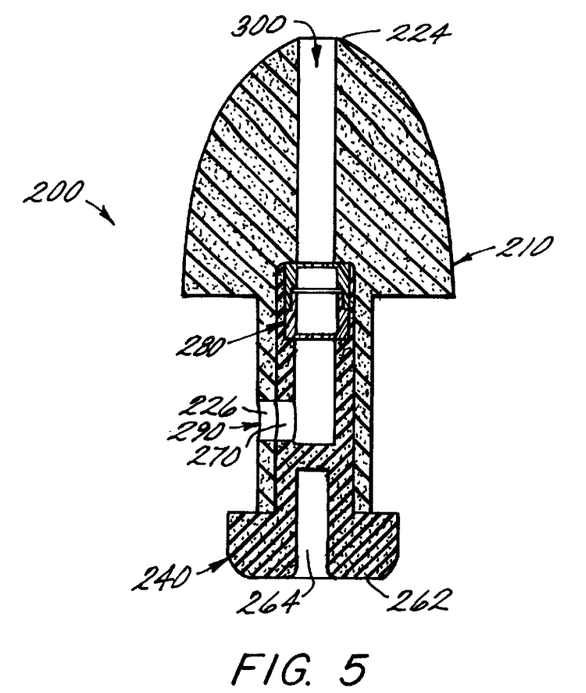
FIG. 5 is a cross-sectional view of another embodiment of the selective nonlinear attenuating earplug in accordance with the present invention.
Figure 6:
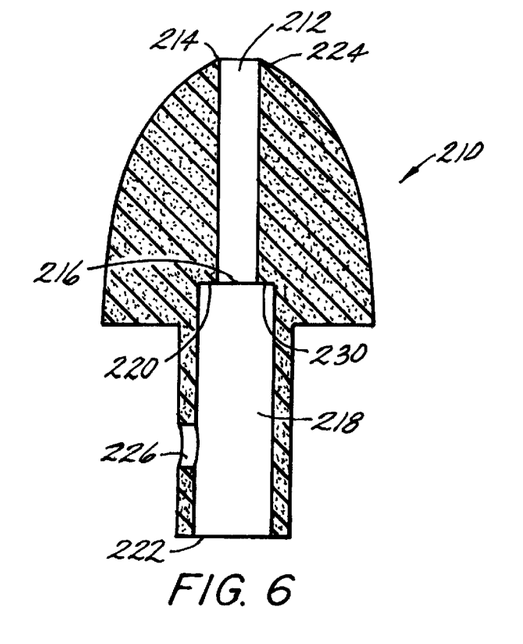
FIG. 6 is a cross-sectional view of the stalk member of the earplug of FIG. 5.
Figure 7:
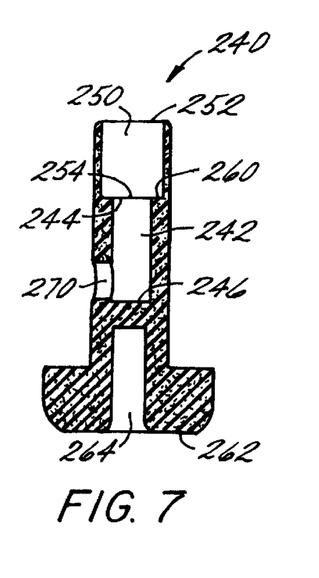
FIG. 7 is a cross-sectional view of the stem of the earplug of FIG. 5.

Now turning to FIGS. 5–7 wherein another embodiment of the selective attenuation earplug of the present invention is provided and is generally designated by the reference numeral 200. Earplug 200 broadly comprises a stalk member 210, a stem 240 and an acoustic filter 280.

Stalk member 210 consists of an elongated member having a stalk passage way 212, a stalk cavity 218 and an annular shoulder 230. Stalk passage way 212 is axially aligned with stalk cavity 218. Stalk passage way has a first end 214 and a second end 216, first end 214 being at a nose end 224 of stalk member 210. Second end 216 is axially aligned with stalk cavity 218 so that stalk passage way 212 communicates with stalk cavity 218. Stalk cavity 218 has a first end 220 which abuts annular shoulder 230 which is formed by stalk member 210. Stalk member 210 also includes a stalk aperture 226.

Stem 240 is an elongated member having a stem passage way 242, a stem cavity 250 and an annular shoulder 260. Stem passage way 242 having a first end 244 and a second end 246 wherein first end 244 communicates and is axially aligned with the stem cavity 250. Second end 246 of stem passage way 242 terminates within the body of the stem 240. Stem cavity 250 has a first end 252 and a second end 254 wherein first end 252 of stem cavity receives acoustic filter 280 and second end 254 is axially aligned and communicates with stem passage way 242. At second end 254 of stem cavity 250 annular shoulder 260 is provided to position acoustic filter 280. Stem cavity 250 is sized to receive acoustic filter 280 and when acoustic filter 280 is inserted into stem cavity 250, acoustic filter 280 rests on annular shoulder 260 axially aligned with the stem passage way 242.

Stem 240 also includes stem aperture 270 and a free end 262 opposite stem cavity 250. At free end 262, stem 240 may contain an axially orientated channel or aperture 264 of a size adapted to receive the end of a length of pliant cord therein. The pliant cord may be used to conventionally hold together the two earplugs.

Stem 240 is rotatably coupled with stalk member 210 by inserting first end 252 of stem cavity 250 into stalk cavity 218 until first end 252 contacts annular shoulder 230 of stalk member 210. When first end 252 abuts annular shoulder 230 of stalk member 210, annular shoulder 230 acts as a stop and positions the acoustic filter 280 within stem cavity 250 and relative to stem passage way 242 so that axially alignment results between the acoustic filter 280 and stem passage way 242 and stalk passage way 212. This axially alignment between acoustic filter 280, stem passage way 242 and stalk passage way 212 forms sound channel 300 of earplug 200. When stem 240 is properly inserted into stalk cavity 218, acoustic filter 280 is positioned between annular shoulder 230 of stalk member 210 and annular shoulder 260 of stem 240.

Sound channel 300 is a contiguous channel formed by stalk passage way 212, stem passage way 242 and acoustic filter 280. Preferably, stalk passage way 212, stem passage way 242, stalk cavity 218 and stem cavity 250 are cylindrical in nature; however, it is within the scope of this invention that the passage ways and cavities may take the form of other suitable shapes and dimensions. In an exemplary embodiment, the diameter of stalk passage way 212, stem passage way 242, inlet aperture 290 and sound channel 300 is between about 0.073 inches and about 0.076 inches.

Selective attenuation earplug 200 of this embodiment also includes an inlet aperture 290 which permits sound waves to enter sound channel 300 from the environment. Inlet aperture 290 is defined by stalk aperture 226 and stem aperture 270 and is functional only in a first orientation when stalk aperture 226 and stem aperture 270 are axially aligned thereby permitting sound waves to travel into sound channel 300. In a second orientation when the stalk aperture 226 and stem aperture 270 are not axially aligned, the inlet aperture 290 is not functional and maximum attenuation results. Inlet aperture 290 is generally perpendicular to sound channel 300.

By being rotatably mounted to stalk member 210, stem 240 regulates the sound channel 300 as disclosed previously herein. Earplug 300 is tunable by the wearer and permits the wearer the option to select the desired performance of the earplug. If the wearer desires for earplug 200 to function in a selective attenuation mode, the wearer simply rotates stem 240 so that stem aperture 270 is axially aligned with stalk aperture 226 to form inlet aperture 290. Due to the axially alignment of the stem passage way 242, acoustic filter 280 and the stalk passage way 212, sound waves are effectively attenuated before passing into the wearer's ear canal. When the wearer desires earplug 200 to function in a maximum attenuation mode, the wearer prevents sound waves from entering sound channel 300 by closing the sound channel 300 by turning free end 262 of the stem ninety degrees (90°) relative to the stalk member 210 thereby causing stem aperture 270 to be skewed from stalk aperture 226. By preventing sound waves from entering the inlet aperture 290, earplug 200 effectively limits the entry of all sound waves into the eardrum.

In accordance with the present invention, acoustic filter 280 for use with earplug 200 may comprise any suitable acoustic filter and preferably comprises the acoustic filter of FIG. 4 as previously disclosed herein.

The stalk member 210 of earplug 200 comprises a soft resilient polymeric foam adapted in size and shape to be inserted into the human ear canal in acoustically obturating relationship therewith. In one embodiment, stalk member 210 is composed of a molded polyurethane foam formed in accordance with U.S. Pat. No. 5,188,123. In other embodiments, stalk member 210 is composed of suitable thermoplastic compositions known in the art.

Stem 240 of earplug 200 is preferably composed of a resilient polymeric material of the same type disclosed herein with respect to earplug 10 of FIGS. 1–3. Preferably, stem 240 of the present invention is manufactured by using details set forth in U.S. Pat. No. 4,867,149 and by using conventional molding techniques known in the art.

Figure 9A:
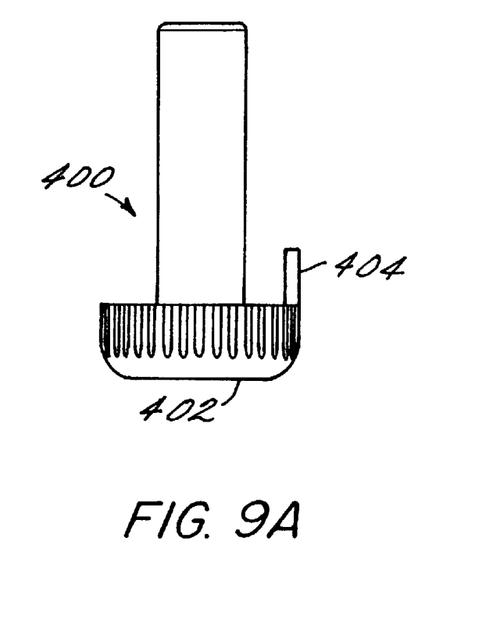
FIG. 9A is perspective view of another embodiment of the stem; wherein the stem has a protrusion.
Figure 9B:
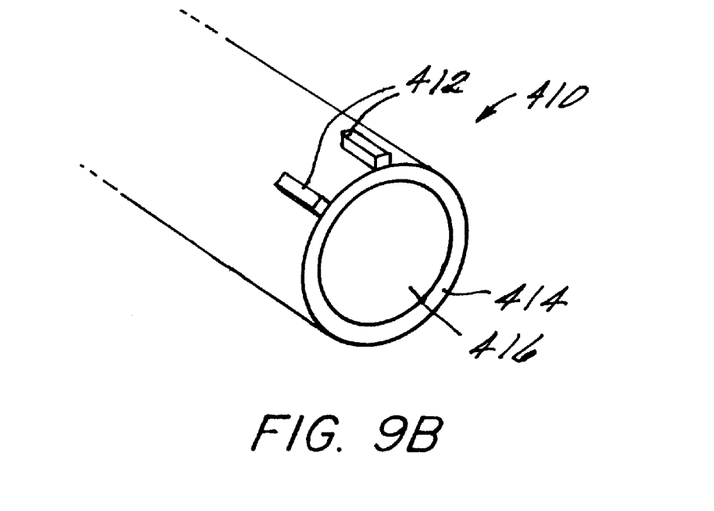
FIG. 9B is a partial perspective view of an embodiment of the stalk member intended to be used with the stem of FIG. 9A.

Turning now to FIGS. 9A–B, another embodiment of the present invention is shown. Stem 400 and stalk member 410 are similar to stem 14 and stalk member 12 of FIGS. 1–3 and disclosed herein; except that stem 400 has a protrusion 404 at free end 402 and stalk member 410 has a pair of stoppers 412 disposed on the outer surface of the stalk member at the second end 414 of the stalk cavity 416. Stoppers 412 are disposed on the outer surface at and angle of approximately 45° relative to one another. When stem 400 is inserted into stalk cavity 416, protrusion 404 is provided between stoppers 416 as stem 400 is properly engaged with stalk member 410 as disclosed hereinbefore. Stoppers 416 serve to facilitate the user in tuning the earplug from a selective mode to a maximum mode or vice versa. Stoppers 416 limit the rotatability of stem 400 and therefore permit the user to more easily axially align the stem aperture (not shown) with the stalk aperture (not shown).

While preferred embodiments have been shown and described, various modifications and substitutions may be made thereto without departing from the spirit and scope of the invention. Accordingly, it is understood that the present invention has been described by way of illustrations and not limitation.

What is claimed is:

1. A hearing protector earplug capable of selectively attenuating noises comprising:

an assembly which includes selectively engageable parts for manual adjustment between at least a first orientation and a second orientation so as to selectively attenuate noises; wherein the assembly includes:

a stalk member having a stalk aperture;

a stem having a stem aperture;

a sound channel through the stalk member and the stem; and wherein the stem is rotatably coupled to the stalk member and in the first orientation the stem aperture and the stalk aperture are axially aligned to form an inlet aperture in the sound channel and in the second orientation the stem aperture and the stalk aperture are not axially aligned.

2. The hearing protective earplug of claim 1 further including:

an acoustic filter disposed within the sound channel.

3. The hearing protective earplug of claim 2, wherein the stalk member includes a stalk passage way therein, a stalk cavity and an annular shoulder formed at one end of the stalk cavity and the stem includes a stem passage way therein, a stem cavity and an annular shoulder formed at one end of the stem cavity.

4. The hearing protective earplug of claim 3, wherein the sound channel is a continuous channel formed by the stalk passage way, the stem passage way and the acoustic filter.

5. The hearing protector earplug of claim 3, wherein the stem is rotatably coupled to the stalk member by inserting the stem into the stalk cavity whereby the stem abuts the annular shoulder of the stalk member.

6. The hearing protective earplug of claim 3, wherein the stalk passage way and stalk cavity are axially aligned with one another whereby one end of the stalk passage way communicates with one end of the stalk cavity, and the stem passage way and stem cavity are axially aligned with one another whereby one end of the stem passage way communicates with one end of the stem cavity.

7. The hearing protective earplug of claim 3, wherein the acoustic filter is disposed between the annular shoulder of the stem and the annular shoulder of the stalk member when the stem is rotatably coupled with the stalk member.

8. The hearing protective earplug of claim 2, wherein the acoustic filter comprises:

a cylindrical body having a first closed opening and a second closed opening, the first closed opening having a first aperture and the second closed opening having a second aperture.

9. The hearing protective earplug of claim 1, wherein the first orientation comprises a selective attenuation mode of the earplug and the second orientation comprises a maximum attenuation mode.

10. The hearing protective earplug of claim 1, wherein the inlet aperture is essentially perpendicular to the longitudinal axis of the sound channel.

11. The hearing protective earplug of claim 1, including at least one flange extending from the assembly for engagement with the ear.

12. The hearing protective earplug of claim 11, wherein at least one flange comprises:
   a plurality of flanges.
13. The hearing protective earplug of claim 12, including:
   at least three flanges.
14. The hearing protective earplug of claim 13, wherein the flanges have a conical, hemispherical or arcuate shape.
15. The hearing protective earplug of claim 13, wherein the stalk member has a nose end and the stalk member further includes a flange array comprising at least three hollow, rearwardly extending flange elements of substantially circular crossections and of serially increasing diameters integrally affixed to the stalk member at spaced intervals along at least a portion of the length thereof, the flange element of the smallest diameter being located at the nose end.
16. The hearing protective earplug of claim 1, wherein the earplug is composed, at least in part, of a material selected from the group consisting of thermoplastic silicone rubber, natural rubber, neoprene rubber, SBR rubber, EPDM rubber, polybutadiene rubber, polyurethane elastomers, ethylene vinyl acetate elastomers, elastomers based on acrylic acid precursors and vinyl halide polymers.
17. The hearing protective earplug of claim 1, wherein the stem has a free end with an aperture therein for receiving a chord.
18. The hearing protective earplug of claim 17, wherein the free end has a plurality of ribs.
19. The hearing protective earplug of claim 17, wherein the free end has an outer dimension greater than the outer dimension of the stalk member.
20. The hearing protective earplug of claim 1, wherein the assembly includes:
   a foam portion for engagement with the ear.
21. The hearing protective earplug of claim 1, wherein the stalk member comprises a soft, resilient polymeric foam body.
22. The hearing protective earplug of claim 21, wherein the foam body is composed of polyurethane.
23. A method of selectively attenuating sound in an earplug comprising:
   providing a stalk member having a stalk passage way and a stalk aperture;
   providing a stem having a stem passage way, stem cavity and stem aperture;
   inserting the stem into the stalk cavity; and
   rotating the stem relative to the stalk member to change the attenuation of the earplug.
24. The method of claim 23, wherein the stalk member includes a stalk cavity therein and the stem includes a stem cavity therein whereby a sound channel is formed by the stalk passage way, stalk cavity, stem cavity and stem passage way.
25. The method of claim 24, wherein the stem is rotated to axially align the stem aperture with the stalk aperture to form an inlet aperture and provide a selective attenuation mode and wherein the stem is rotated to not axially align the stem aperture to the stalk aperture to provide a maximum attenuation mode, the inlet aperture communicating with the sound channel.
26. The method of claim 23, further comprising:
   inserting an acoustic filter into the stem cavity prior to inserting the stem into the stalk cavity.
27. The method of claim 23, wherein the stem has a free end with an outer dimension greater than the outer dimension of the stalk member.

* * * * *